United States Patent [19]

Fishman

[11] Patent Number: 5,154,181

[45] Date of Patent: * Oct. 13, 1992

[54] ALLERGY TESTING METHOD AND APPARATUS

[76] Inventor: Henry Fishman, 5173 Linnean Ter. NW., Washington, D.C. 20008

[*] Notice: The portion of the term of this patent subsequent to Jul. 2, 2008 has been disclaimed.

[21] Appl. No.: 685,626

[22] Filed: Apr. 15, 1991

Related U.S. Application Data

[63] Continuation of Ser. No. 501,376, Mar. 29, 1990, Pat. No. 5,027,826, which is a continuation of Ser. No. 339,863, Apr. 14, 1989, abandoned, which is a continuation of Ser. No. 204,967, May 31, 1988, abandoned, which is a continuation of Ser. No. 88,139, Aug. 21, 1987, abandoned, which is a continuation of Ser. No. 853,710, Apr. 18, 1986, Pat. No. 4,711,247.

[51] Int. Cl.⁵ ............................................ A61B 5/00
[52] U.S. Cl. ........................... 128/743; 604/47; 604/191; 604/201
[58] Field of Search .................. 128/743; 604/46, 47, 604/181, 191, 201, 244, 411, 413

[56] References Cited

U.S. PATENT DOCUMENTS

| 2,841,138 | 7/1958 | Laub . | |
|---|---|---|---|
| 3,289,670 | 12/1966 | Krug | 604/47 |
| 3,999,543 | 12/1976 | Lacey | 604/413 |
| 4,168,701 | 9/1979 | Chiulli | 128/655 |
| 4,270,548 | 6/1981 | Brennan | 128/743 |
| 4,292,979 | 10/1981 | Inglefield et al. | 128/743 |
| 4,453,926 | 6/1984 | Galy | 604/47 |
| 5,027,826 | 7/1991 | Fishman | 604/47 |

FOREIGN PATENT DOCUMENTS

| 913485 | 10/1972 | Canada | 128/743 |
|---|---|---|---|
| 325001 | 10/1902 | France . | |

*Primary Examiner*—Randy C. Shay
*Attorney, Agent, or Firm*—Frishauf, Holtz, Goodman & Woodward

[57] ABSTRACT

An allergy testing method and apparatus for testing a patient for a plurality of allergies at substantially the same time, comprises a carrier for receiving a plurality of allergen applying devices, each allergen applying device including a source of an allergen and a movable pricking needle which is movable from an inactive position out of contact with the skin of a patient to an active position for pricking the skin of a patient and applying its associated allergen to the pricked skin when moved from the inactive position to the active position. The carrier holds and supports the plurality of allergen applying devices with a given spacing between each of the pricking needles, and an actuator is coupled to the carrier for moving the pricking needles from their inactive positions to their active positions to prick or pierce the skin of a patient and to thereby apply a respective allergen to the skin of the patient via the pricking needles.

23 Claims, 3 Drawing Sheets

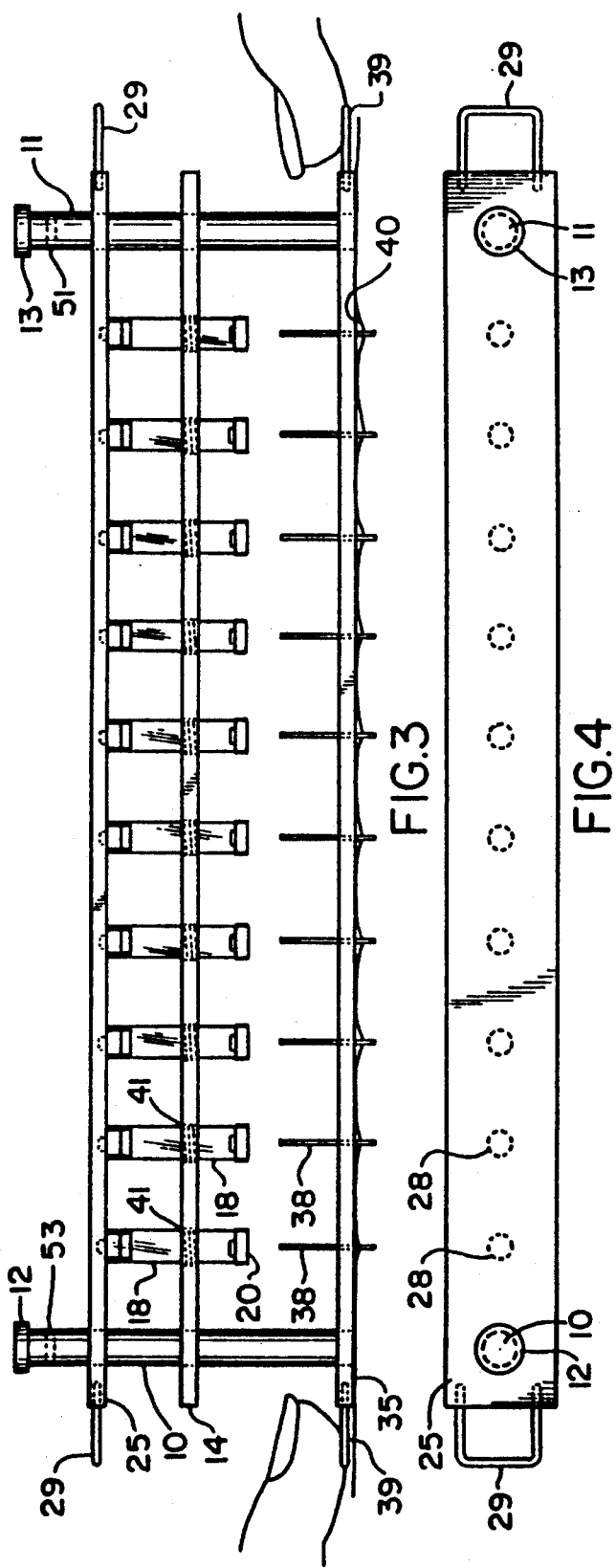
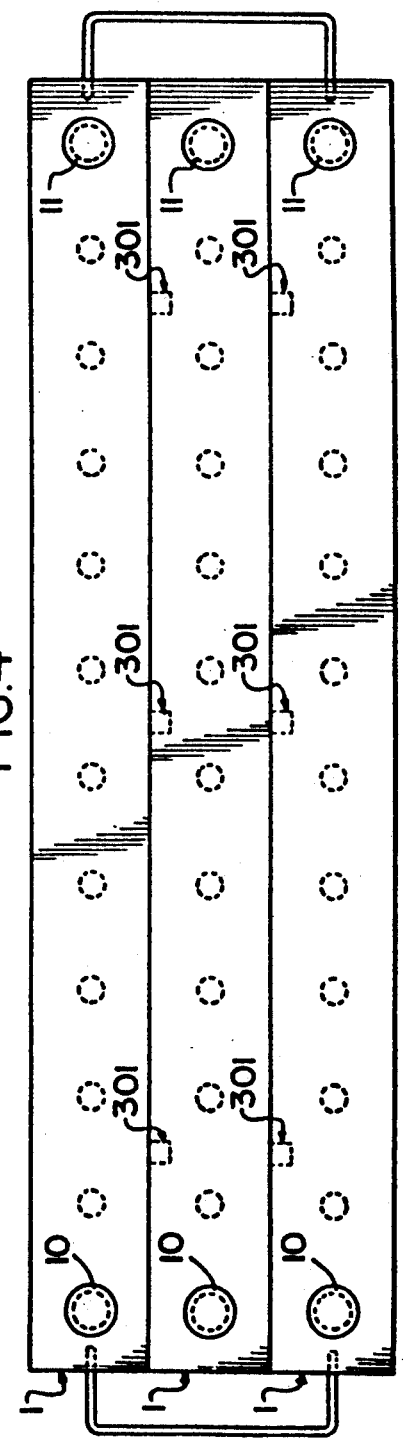
FIG.3
FIG.4
FIG.7

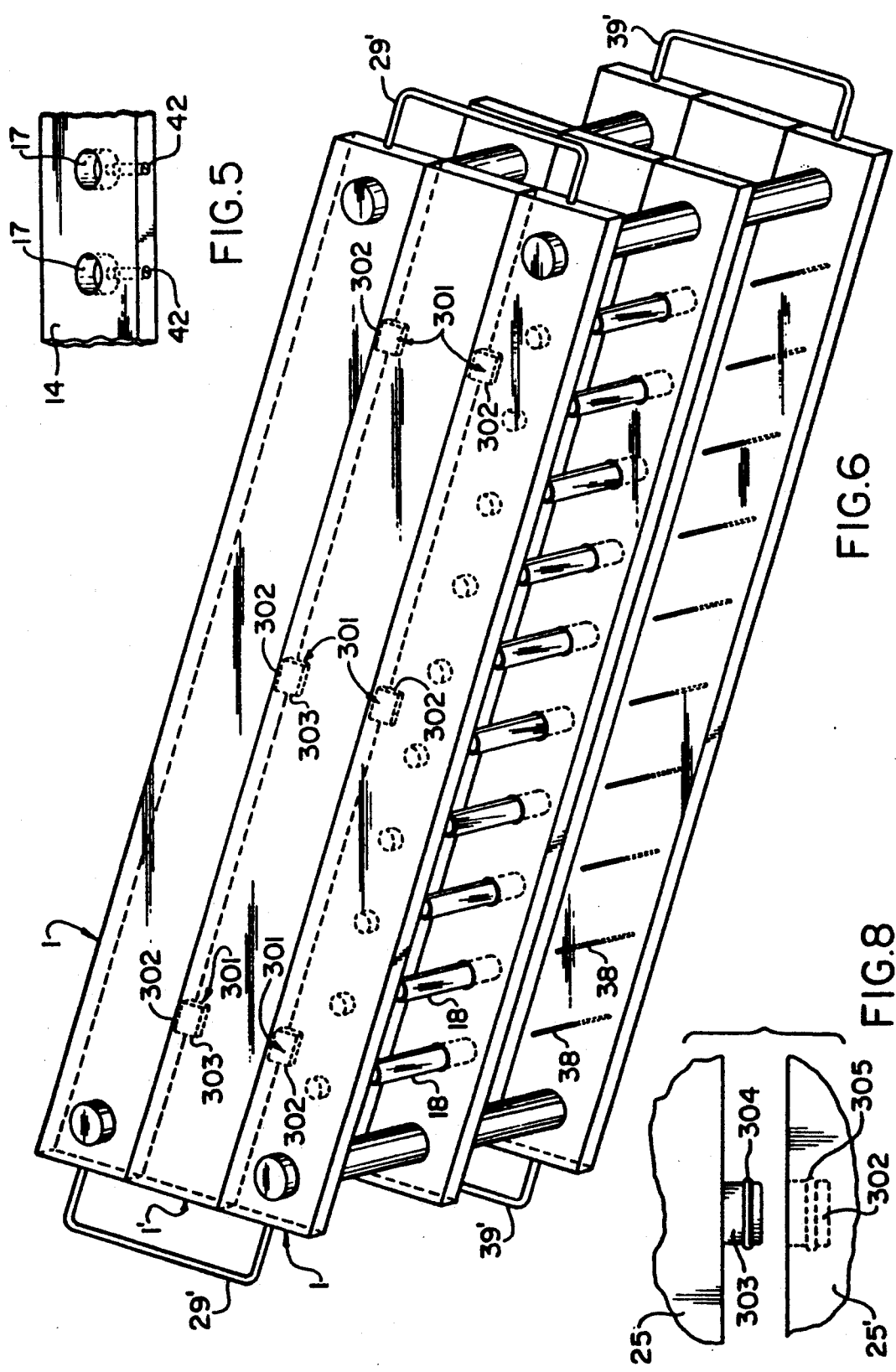

ALLERGY TESTING METHOD AND APPARATUS

This is a continuation of application Ser. No. 07/501,376 filed Mar. 29, 1990 (now U.S. Pat. No. 5,027,826), which in turn is a continuation of Ser. No. 07/339,863 filed Apr. 14, 1989 (abandoned) which in turn is a continuation of Ser. No. 07/204,967 filed May 31, 1988 (abandoned) which in turn is a continuation of Ser. No. 07/088,139 filed Aug. 21, 1987 (abandoned) which in turn is a continuation of Ser. No. 06/853,710 filed Apr. 18, 1986 (now U.S. Pat. No. 4,711,247).

CROSS REFERENCE TO RELATED APPLICATION

U.S. application Ser. No. 06/853748, filed Apr. 18, 1986 in the names of Henry Fishman (the sole inventor in the present application) and Robert Olshaker. Ser. No. 06/853,748 was abandoned in favor of continuation-in-part application Ser. No. 07/113,364 filed Oct. 27, 1987, which was abandoned in favor of continuation application Ser. No. 07/532,239, filed May 29, 1990, which was abandoned in favor of Continuation Application Ser. No. 07/626,236, filed Dec. 11, 1990 (now U.S. Pat. No. 5,076,282).

BACKGROUND OF THE INVENTION

This invention relates to allergy testing methods and apparatuses, and more specifically to improved apparatuses and methods for testing a patient for a plurality of allergies at substantially the same time.

Allergy testing generally involves giving a patient a plurality of "prick tests." Each prick test is applied in order to determine whether or not a patient is allergic to a particular substance, such as pollen, animal dander, dust, foods, etc. A conventional prick test involves placing a drop of a test substance on the patient's skin and then using a needle to scratch the substance through the skin. If a reaction occurs, the patient is considered to be allergic to the particular substance. At present, allergy testing is carried out on an individual basis. Each test substance is dropped, one drop at a time, on the patient's arm or back. Each drop is then individually pricked through the skin with a separate needle. This is a very time consuming process (for both the patient and the practitioner) and very often involves multiple office visits for the patient. This leads also to a substantial amount of patient discomfort, expense, and inconvenience.

An object of the present invention is to provide improved apparatuses and methods for testing patients for allergic reactions to a plurality of substances, all at substantially the same time. The invention will reduce the time required for testing, minimizing patient discomfort, expense and inconvenience, and improving productivity.

A further object of the invention is to provide improved methods and apparatuses which will enable the plurality of allergy tests to be applied simultaneously without requiring a great deal of technical skill on the part of the operator.

Yet another object of the invention is to provide improved apparatuses which used pre-packaged allergen and needles, which are easily insertible in and removable from a carrier, thereby facilitating loading the carrier with predetermined allergens, and improving the sterility of the apparatus.

Still another object is to provide an allergy testing system where the pricking of the skin is always done to a given skin penetration depth which is predictable and which is replicable without requiring highly skilled operators.

SUMMARY OF THE INVENTION

According to an aspect of the invention, an allergy testing apparatus for testing a patient for a plurality of allergies at substantially the same time, comprises carrier means for receiving a plurality of allergen applying means, each allergen applying means including a source of an allergen and a movable pricking means movable from an inactive position out of contact with the skin of a patient to an active position for pricking the skin of a patient and applying its associated allergen to the pricked skin when moved from the inactive position to the active position; said carrier means holding and supporting the plurality of allergen applying means with a given spacing between each of the pricking means; and actuating means coupled to said carrier means for moving the pricking means of each of the allergen applying means from the inactive position to the active position thereof to prick or pierce the skin of a patient and to thereby apply an allergen from a respective allergen applying means to the skin of the patient via the pricking means.

According to another aspect of the invention, an allergy testing method for testing a patient for a plurality of allergies at substantially the same time, comprises providing a plurality of allergen applying means, each including a source of an allergen and movable pricking means for pricking the skin of a patient when moved from an inactive position to an active position; mounting and supporting the plurality of allergen applying means in a support means with a given spacing between each of the pricking means; placing the support means adjacent the skin of a patient; and moving the pricking means of each of the allergen applying means from the inactive position to the active position thereof to prick or pierce the skin of a patient and to thereby apply an allergen from a respective allergen applying means to the skin of the patient via the pricking means.

BRIEF DESCRIPTION OF THE DRAWINGS

FIG. 3 is a side view showing the apparatus of FIGS. 1 and 2 after the needles have pierced or pricked the skin of the patient FIG. 4 is a top view of the embodiment of FIGS. 1-3;

FIG. 5 is a partial view of a modified intermediate plate member;

FIG. 6 is a perspective view of a modified embodiment, including three units of FIGS. 1-4;

FIG. 7 is a top plan view of the embodiment of FIG. 6; and

FIG. 8 is a fractional view of a modified interconnection for use in the embodiment of FIGS. 6 and 7.

DETAILED DESCRIPTION

Figure 1:
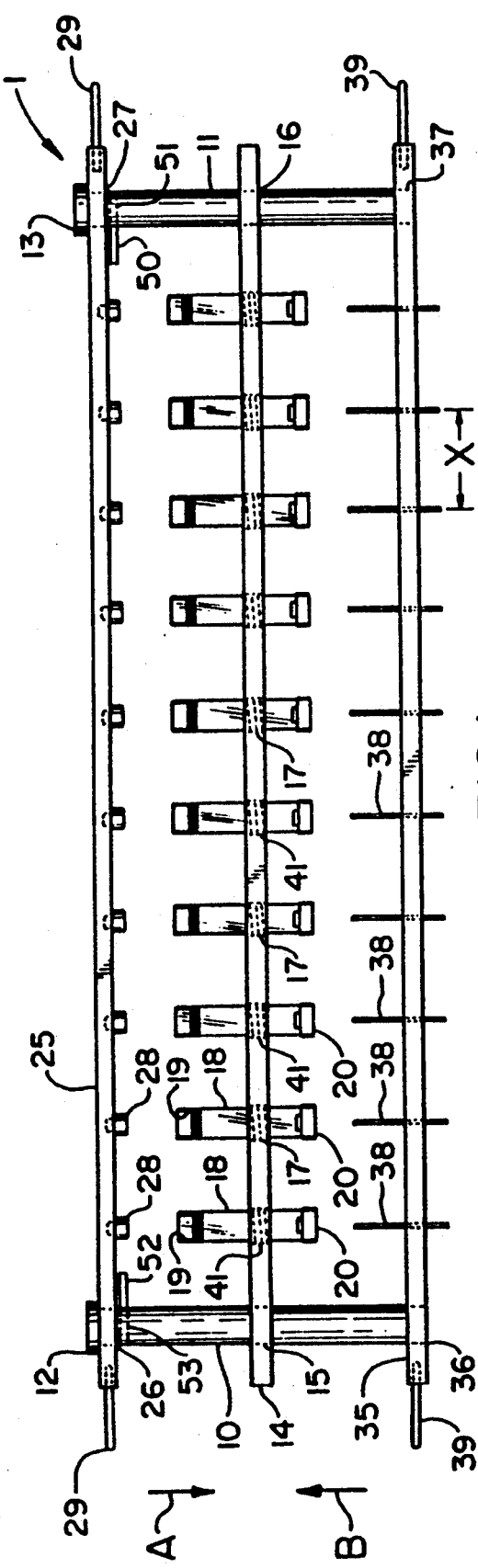
FIG. 1 is a side view, in a partially disassembled state, of an embodiment of the present invention.
Figure 2:
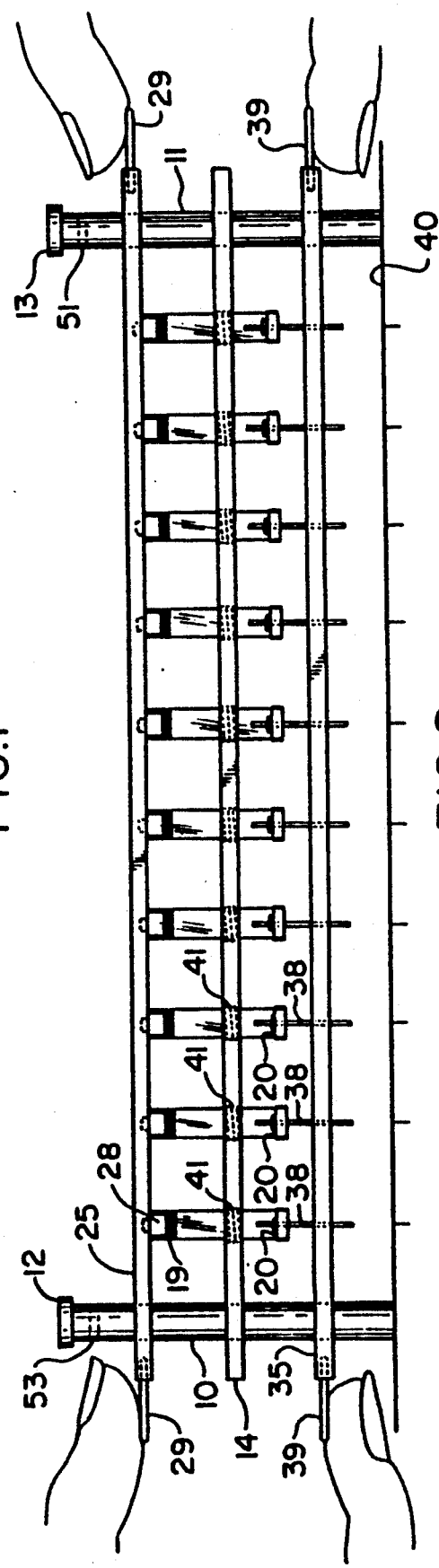
FIG. 2 is a side view of the embodiment of FIG. 1 arranged ready for use.

Referring to FIGS. 1, 2 and 3, an allergy testing unit 1 of the present invention comprises a pair of vertical support posts 10, 11 at opposite ends thereof, the support posts 10, 11 having respective stops 12, 13 at the upper ends thereof. The posts 10, 11 may be made, for example, of plastic material and the end stops 12, 13 can be integrally moulded with the posts 10, 11 respectively. An intermediate plate member 14 has apertures 15, 16 formed at the ends thereof through which the posts 10, 11 respectively pass. The plate number 14 is fixedly connected to and supported by posts 10, 11, for example by an adhesive or the like, in the position shown in FIG. 1. Plate member 14 also comprises a plurality of apertures 17, through which are mounted capsules or vials 18 containing allergens. The capsules 18 have rubber stoppers 19 at the top portions thereof and puncturable rubber seals 20 at the lower portions thereof.

The apparatus further comprises an upper plate member 25 which has apertures 26, 27 therein so as to be slidably mountable on posts 10, 11. If the stops 12, 13 are integrally formed on posts 10, 11, the upper plate is mounted on posts 10, 11 from the bottom, before the intermediate plate 14 is fixed to the posts 10, 11. The upper plate member 25 comprises engaging projecting members 28 which respectively engage into recesses in the upper rubber stopper members 19 of the respective capsules 18, as shown in FIGS. 2 and 3. Upper plate member 25 also comprises handle members 29 at the opposite ends thereof to facilitate handling and griping of the apparatus in use.

The apparatus further comprises a lower plate member 35 having apertures 36, 37 by means of which the lower plate member 35 is slidably mounted on posts 10, 11. Lower plate member 35 has a plurality of hollow needles 38 fixedly mounted therein, the needles 38 preferably having sharp tips at both opposite ends thereof. The needles 38 are mounted in registration with the capsules 18 and projecting members 28. Lower plate member 35 further comprises handles 39 projecting from the opposite ends thereof, similar to the handles 29 of the upper plate member 25 and in registration with handles 29 of upper plate member 25.

As seen in FIG. 1, removable pins 50,52 may be inserted in holes 51,53, respectively, in posts 10,11 to "lock" the upper plate member 25 in its uppermost position. When ready for use, the pins 50,52 may be merely removed by the operator by pulling them out of their respective holes in the posts. Similar pins and holes can be provided in posts 10,11 above the lower plate member 35 in order to physically prevent the lower plate member 35 from moving upwardly, to inadvertently pierce the punctuable rubber seals 20. When ready for use, the pins can, of course, be removed. Other types of locking arrangements could be used in place of pins 50,52 and respective holes 51,53.

FIG. 1 shows the apparatus in its partially assembled state. In operation, the upper plate member 25 is pressed downwardly in the direction of arrow A in FIG. 1, and the lower plate member 35 is pressed upwardly in the direction of the arrow B in FIG. 1 by means of pressing with the fingers of the operator, as shown in FIG. 2, until the apparatus reaches the condition shown in FIG. 2. When the apparatus is in the condition shown in FIG. 2, the posts 10, 11 are placed against the skin 40 of the patient to support the apparatus against the patient's skin, as shown in FIG. 2. In the FIG. 2 condition, the needles 38 are pierced through the respective puncturable seals 20 at the lower portions of the respective capsules 18 and extend into the respective capsules and in contact with the allergens contained with the respective capsules 18. Then, the operator presses the lower plate member 35 downwardly toward the skin 40 as shown in FIG. 3. While pressing downwardly, the needles 38 leave the respective capsules 18 and prick the skin of the patient at predetermined spaced intervals corresponding to the positions at which the needles 38 are fixedly mounted in the lower plate member 35. The allergens which passed into the respective hollow needles 38 are now applied to the pierced or pricked portions of the patient by capillary action. At this point, the upper portion of the unit 1, comprising the posts 10, 11, the upper plate member 25 and the intermediate member 14, can be removed by the operator. The lower plate member 35 can be removed with the other elements of the device or it can remain against the skin of the user for the desired amount of time to permit penetration of the allegen through the needles 38 and into the skin of the patient. After use, the lower plate member 35 along with its needles 38 can either be discarded or sterilized for re-use.

Preferably, the pucturable seals 20 at the lower portions of the respective capsules 18 are of the type that sealingly reclose upon removal of the needle 38 therefrom. Such seals are well known. Thus, the capsules 18 containing the allergens can be re-used with either a new (sterilized) lower plate member 35 and corresponding new needles 38, or a sterilzied re-used lower plate member 35 with its associated sterilized needles 38.

The needles 38 have a given length such that as the lower plate is moved downwardly toward the skin 40, the upper parts of the needles 38 leave the capsules 18 before the lower parts of the needles 38 prick the patient's skin. Thus, the allergens in the capsules 18 do not become contaminated since the needles are free of the capsules 18 when the skin is pricked, and the capsules 18 and the upper part of the assembly can be re-used without sterilization.

The capsules 18 are preferably removably mounted in the intermediate plate 14, for example via screw threads 41 at the intermediate portions of the capsule 18 as illustrated in the FIGS. 1-3. Alternatively, the capsules 18 may be press fit in a tight sliding manner into the apertures in the intermediate plate 14, or may be held in place by means of an adhesive. Preferably, such an adhesive is the type which can be easily broken to permit removal of the capsules 18 from plate 14, and replacement, as desired. As another alternative, respective set screws 42 can be provided on intermediate plate member 14 for each of the capsules 18, as shown in FIG. 5. After insertion of a capsule 18 into an aperture 17, the set screw 42 is tightened against the side of the capsule 18 to hold it in place. A similar set screw arrangement can be used to fix the intermediate plate 14 to the posts 10, 11.

Preferably, the upper closure member 19 of the capsules 18 is resilient rubber or other suitable resilient material so that when the projecting members 28 are received therein and pressure is downwardly applied, the upper closure 19 will yield downwardly and will create pressure inside the capsule 18 to enhance transfer of the allergen out of the capsule, through the hollow needle 38 pierced therein (see FIG. 2) and onto the skin of the user when the device is in the condition shown in FIG. 3.

A plurality of units 1 can be stacked side-by-side, as shown in FIG. 6. In FIG. 6, the outer units 1 are substantially identical to the units 1 of FIGS. 1-4. The middle unit 1' in FIG. 6 is also substantially identical to unit 1 of the embodiment of FIGS. 1-4, except that posts 10, 11 are not required in the middle unit. However. the middle unit 1 could be provided with posts 10, 11, as in the outer units 1. In the embodiment of FIG. 6, each unit 1, 1' comprises ten capsules 18, so that each unit enables ten allergy prick tests to be applied at the same time. The capsules of each unit may contain different allergens, thus enabling a prick test for up to thirty different substances to be applied at the same time, greatly enhancing efficiency. While each unit 1, 1' of the apparatus is described as having ten capsules each containing different allergens, a different number of capsules can be provided in each unit, as desired. The number of units which are connected together side-by-side, may be other than three. For example, the number of units connected together side-by-side is a function of the body area of the patient on which the test is to be performed. For example, if the test is to be performed on the arm of a patient, perhaps only one or two units 1 arranged side-by-side can be used. However, when the test is to be performed on the back of the patient, which is a relatively flat surface, three units or more 1, 1' connected together side-by-side can be advantageously used in some cases.

In FIG. 6, each side of the combined apparatus comprises a single upper handle 29' and a single lower handle 39' which extend between the outermost units 1. The side-by-side units are interconnected by means of male and female sockets and projections which cooperate to form respective interconnections 301. For example, the outer units 1 can comprise recesses 302 in the side walls thereof, and the intermediate unit 1' can comprise projections 303 extending from the side walls thereof for mating with the recesses 302. By providing such an arrangement, the center unit can be a special center unit, and the two outer units can be identical. Alternatively, the projections 303 can be provided on the side walls of the outer units 1, and the intermediate unit 1' can have recesses 302 for receiving the projections 303. Similar interconnections 301 are provided for the intermediate and/or lower plate members of the apparatus, in substantially the same manner as shown for the upper plate member. Alternatively, the units 1, 1' can be adhered together in the side-by-side relation, for example, by means of an adhesive or a solvent (if the plates are made of a suitable plastic material), or they may be otherwise connected for example by screws.

FIG. 7 shows a top view of an embodiment similar to the embodiment of FIG. 6, but wherein each of the units 1 comprises respective posts 10, 11. In FIG. 7, the interconnections 301 are shown as respective male-female (projection-recess) interconnections wherein the projections project from the upper and intermediate units, and the recesses are in the lower and intermediate units 1, as seen in FIG. 7.

The interconnections 301 in FIGS. 6 and 7 may be of the press-fit or interference-fit type to improve the integrity of the interconnection. Snap-type connections may also be provided, such as shown in enlarged scale in FIG. 8. In FIG. 8, the projections 303 have a projecting rib 304, and the recesses 302 have a groove 305 therein to snappingly receive the ribs 304. This construction is particularly advantageous when the plate members (including the interconnections 301) are made of plastic material having some resiliency to permit the rib 304 to pass through the recess 302 and "snap" into a respective groove 305.

An advantage of the apparatus of the present invention is that the prick test is conducted at fixed predetermined spaced apart locations on the patient's skin. The spacing between the capsules 18 (and their associated needles 38) is arranged such that a sufficient distance is provided between adjacent needles so that the adjacent prick tests will not interfere with each other. In a preferred embodiment, the spacing "x" between adjacent needles (see FIG. 1) is approximately ½-¾ inch. A similar needle spacing is provided between adjacent needles of side-by-side connected units in the direction perpendicular to the direction "x" in FIG. 1. This eliminates the problem that respective prick tests may be applied too close to each other.

Preferably, the plate members 14, 25, 35 and the posts 10, 11 are fabricated of sterilizable plastic material, such as polyvinylchloride (PVC).

The capsules 18 are preferably made of glass or plastic material, and the needles, of course, are preferably made of metal, such as stainless steel.

An important advantage of the present invention is that the pricking or piercing of the skin is always done to a given skin penetration depth. The penetration depth is a function of the distance the needles 38 project downwardly from the lower plate member 35. See FIG. 3. Moreover, the skin penetration depth is replicable without requiring highly skilled operators, since the penetration depth is not a function of the skill of the operator, but is a function of the distance the needles 38 project downwardly from the lower plate member 35. Thus, repeatable results are obtainable when using the system of the present invention.

The upper plate-like member 25 is not absolutely required. The handles 29 can be coupled to the ends of the intermediate plate-like member 14. Handling and operation of the apparatus will be essentially similar to that described hereinabove. Also, the support rods or posts 10,11 need not be round. They may be rectangular, oval or any other convenient shape.

The term "allegen" is used throughout this specification and claims to denote the substance applied to a patient. However, the invention is equally applicable to antigens in general and the term "allergen" as used in the specification and claims denotes antigens as well as allergens.

It should be clear that various modifications and alterations can be made within the scope of the appended claims.

I claim:
1. An allergy testing apparatus for testing a patient for a plurality of allergies at substantially the same time, comprising:
a plurality of sources of an allergen;
a common allergen carrying means for carrying said plurality of sources of an allergen with said allergen sources in spaced apart relationship;
a plurality of spaced apart movable pricking means mounted on a common movable member so as to be movable as a unit with said common movable member;
carrier means including means for supporting said movable member such that said movable member and said pricking means mounted thereon are substantially simultaneously movable relative to said carrier means along a substantially fixed predetermined path from an inactive position out of contact with the skin of a patient to an active position for pricking the skin of a patient, each of said pricking means being arranged for applying allergen from a respective allergen source to the pricked skin when moved along said path from said inactive position to said active position;

said carrier means including means for at least partially defining said substantially fixed predetermined path in cooperation with said movable member; and actuating means, coupled to said movable member, for (i) moving said movable member and said pricking means substantially simultaneously relative to said carrier means for causing each of said pricking means to contact a respective allergen source and to retain a respective allergen thereon, and for (ii) moving said movable member and said pricking means substantially simultaneously relative to said carrier means along said path from said inactive position to said active position thereof, for thereby substantially simultaneously applying allergens retained on respective pricking means at spaced apart positions on the skin of the patient when said respective pricking means reaches said active position.

2. The allergy testing apparatus of claim 1, wherein said sources of an allergen each comprise a receptacle containing an allergen, and wherein said movable pricking means each comprise a movable needle which is movable relative to said receptacles so as to be in communication with the interior of an associated receptacle so as to contact the respective allergen.

3. The allergy testing apparatus of claim 2, wherein each of said needles is hollow and said receptive allergen passes through the hollows of said needles by capillary action.

4. The allergy testing apparatus of claim 2, wherein said common carrying means comprises an elongated member for carrying and receiving a plurality of said sources of allergen.

5. The allergy testing apparatus of claim 1, wherein said common carrying means comprises an elongated member for carrying and receiving a plurality of said sources of allergen.

6. The allergy testing apparatus of claim 1, wherein said movable pricking means, in said active position thereof, is out of communication with said sources of an allergen, thereby preventing contamination of said sources of allergen due to contact of said pricking means with the skin of a patient.

7. The allergy testing apparatus of claim 1, wherein:
said carrier means comprises at least first and second members which are movable relative to each other;
one of said first and second members comprising an elongated member carrying said plurality of pricking means;
the other of said first and second members including support means for supporting said elongated member, said support means being adapted to be placed on the skin of a patient and spacing said pricking means from said skin in said inactive position; and said elongated member carrying said plurality of pricking means being movably coupled to said support means for moving said plurality of pricking means to said active position.

8. The allergy testing apparatus of claim 7, wherein said movable pricking means, in said active position thereof, is out of communication with said sources of an allergen, thereby preventing contamination of said sources of allergen due to contact of said pricking means with the skin of a patient.

9. The allergy testing apparatus of claim 7, wherein said sources of an allergen each comprise a receptacle containing an allergen, and wherein said movable pricking means each comprise a movable needle which is movable relative to said receptacles so as to be in communication with the interior of an associated receptacle so as to contact the respective allergen.

10. The allergy testing apparatus of claim 9, wherein said needles extend from said elongated member by a predetermined distance, whereby said needles prick the skin of the patient to a predetermined controlled depth of penetration at said second position of said elongated member.

11. The allergy testing apparatus of claim 1, wherein said actuating means includes means for moving said plurality of pricking means to prick the skin of the patient in said active position to a predetermined controlled depth of penetration.

12. A a method of testing a patient for a plurality of allergies at substantially the same time, comprising:
providing a plurality of allergens in a common allergen carrying means for carrying said plurality of allergens with said allergens in mutually spaced apart relationship;
providing a plurality of spaced apart movable pricking means mounted on a common movable member so as to be movable as a unit with said common movable member;
supporting said movable member on a carrier such that said movable member and said pricking means mounted thereon are substantially simultaneously movable relative to said carrier along a substantially fixed predetermined path from an inactive position out of contact with the skin of a patient to an active position for pricking the skin of a patient, each of said pricking means being arranged for applying a respective allergen from said common allergen carrying means to the pricked skin when moved to said active position;
at least partially defining said substantially fixed predetermined path by said carrier in cooperation with said movable member;
moving said movable member with said pricking means thereon substantially simultaneously relative to said carrier for causing each of said pricking means to contact a respective allergen and to retain the respective allergen thereon; and
moving said movable member with said pricking means thereon substantially simultaneously relative to said carrier along said path from said inactive position to said active position thereof, for thereby substantially simultaneously applying allergens retained on respective pricking means at spaced apart positions on the skin of the patient when said respective pricking means reach said active position.

13. The allergy testing method of claim 12, comprising providing said common allergen carrying means with a plurality of receptacles each containing an allergen, and wherein said movable pricking means each comprise a movable needle which is movable with said movable member so as to be in communication with the interior of an associated receptacle to contact said respective allergens.

14. The allergy testing method of claim 13, wherein each of said needles is hollow and comprising passing said receptive allergen through the hollows of said needles by capillary action.

15. The allergy testing method of claim 13, comprising providing said common carrying means with an elongated member for carrying and receiving a plurality of said sources of allergen.

16. The allergy testing method of claim 12, comprising providing said common carrying means as an elongated member for carrying and receiving a plurality of said sources of allergen.

17. The allergy testing method of claim 12, comprising maintaining said movable pricking means, in said active position thereof, out of communication with said allergens, thereby preventing contamination of said allergens due to contact of said pricking means with the skin of a patient.

18. The allergy testing method of claim 12, wherein:
said carrier comprises at least first and second members which are movable relative to each other;
one of said first and second members comprises an elongated member carrying said plurality of pricking means;
the other of said first and second members includes support means for supporting said elongated member, said support means being adapted to be placed on the skin of a patient and maintaining said pricking means spaced from said skin in said inactive position; and
comprising moving said elongated member carrying said plurality of pricking means is relative to said support means for causing moving of said plurality of pricking means to said active position.

19. The allergy testing method of claim 18, comprising maintaining said movable pricking means, in said active position thereof, out of communication with said allergens, thereby preventing contamination of said allergens due to contact of said pricking means with the skin of a patient.

20. The allergy testing method of claim 18, comprising providing said common allergen carrying means with a plurality of receptacles each containing an allergen, and wherein said movable pricking means each comprise a movable needle which is movable with said movable member so as to be in communication with the interior of an associated receptacle to contact said respective allergens.

21. The allergy testing method of claim 20, wherein said needles extend from said elongated member by a predetermined distance, and said needles prick the skin of the patient to a predetermined controlled depth of penetration at said second position of said elongated member.

22. The allergy testing method of claim 12, wherein said step of moving said plurality of pricking means to prick the skin of the patient in said active position comprises moving said pricking means to a predetermined controlled depth of penetration.

23. An allergy testing apparatus for testing a patient for a plurality of allergies at substantially the same time, comprising:
a plurality of sources of an allergen;
a common allergen carrying means for carrying said plurality of sources of an allergen with said allergen sources in spaced apart relationship;
a plurality of spaced apart movable pricking means mounted on a common movable member so as to be movable as a unit with said common movable member;
carrier means including means for contacting the skin of a patient and supporting said movable member relative to the skin of a patient such that said movable member and said pricking means mounted thereon are substantially simultaneously movable along a substantially fixed predetermined path from an inactive position out of contact with the skin of the patient to an active position for pricking the skin of a patient, each of said pricking means being arranged for applying allergen from a respective allergen source to the pricked skin when moved along said path from said inactive position to said active position;
said carrier means including means for at least partially defining said substantially fixed predetermined path in cooperation with said movable member; and
actuating means, coupled to at least one of said movable member and carrier means, for
(i) moving said movable member and said pricking means substantially simultaneously relative to said allergen carrying means for causing each of said pricking means to contact a respective allergen source and to retain a respective allergen thereon, and for
(ii) moving said movable member and said pricking means substantially simultaneously, relative to said skin of said patient which adapted to be contacted by said carrier means, along said path from said inactive position to said active position thereof, for thereby substantially simultaneously applying allergens retained on respective pricking means at spaced apart positions on the skin of the patient when said respective pricking means reaches said active position.

* * * * *